United States Patent

Matsumura

[11] 4,283,124
[45] Aug. 11, 1981

[54] EYE FUNDUS CAMERA

[75] Inventor: Isao Matsumura, Yokohama, Japan

[73] Assignee: Canon Kabushiki Kaisha, Tokyo, Japan

[21] Appl. No.: 945,845

[22] Filed: Sep. 26, 1978

Related U.S. Application Data

[63] Continuation of Ser. No. 587,661, Jun. 17, 1975, abandoned.

[30] Foreign Application Priority Data

Jun. 19, 1974 [JP] Japan ................................ 49/69949

[51] Int. Cl.³ ............................................. A61B 3/10
[52] U.S. Cl. ..................................................... 351/7
[58] Field of Search .......................... 351/7, 9, 13, 16; 354/62

[56] References Cited

U.S. PATENT DOCUMENTS

| 2,327,612 | 8/1943 | Stone et al. ............................. 351/7 |
| 3,089,398 | 5/1963 | Wilms .................................. 351/7 X |
| 3,217,622 | 11/1965 | Kujono ................................ 351/7 X |
| 3,259,039 | 7/1966 | Okajima ................................ 351/7 |
| 3,259,041 | 7/1966 | Okajima ............................. 351/7 X |
| 3,594,071 | 7/1971 | Okajima ................................ 351/7 |
| 3,598,107 | 8/1971 | Ishikawa et al. .................... 351/7 X |
| 3,614,214 | 10/1971 | Cornsweet et al. .................... 351/7 |
| 3,777,738 | 12/1973 | Sugita et al. ....................... 351/7 X |
| 3,791,719 | 2/1974 | Kratzer et al. ...................... 351/9 X |
| 3,925,793 | 12/1975 | Matsumara et al. ................. 351/7 X |

FOREIGN PATENT DOCUMENTS

1127947 12/1956 France ........................................ 351/7

Primary Examiner—Paul A. Sacher
Attorney, Agent, or Firm—Toren, McGeady and Stanger

[57] ABSTRACT

An eye fundus camera illuminates the eye to be inspected with a light that does not cause dilation or contraction of the eye pupil. In the camera, a photographic system forms an image of the eye fundus on a recording body. A projection system projects an image, of infrared light, or predetermined shape on the eye fundus. An observation system observes the image. Focusing means permit focusing the eye fundus image on the recording body at the same time as the image of the mark is formed on the eye fundus. The system is focused by operating the focusing means to focus an image of the mark.

30 Claims, 8 Drawing Figures

EYE FUNDUS CAMERA

This is a continuation of Application Ser. No. 587,661 filed on June 17, 1975 and now abandoned.

BACKGROUND OF THE INVENTION

The present invention relates to a camera for taking picture of the eye fundus and particularly to an eye fundus camera, which is equipped with a mechanism for illuminating the eye to be inspected without causing the dilation and the contraction of eye pupil.

Roughly speaking, there are two kinds of eye fundus cameras. One illuminates the eye with visible light to permit focusing. The other illuminates the eye with light such as infrared light which does not cause dilation or contraction of the eye pupil. In the first case it is necessary to apply a pupil dilating agent to the eye in order to avoid contraction of the pupil in response to visible light. However, this agent not only bothers the patient but also creates the danger of damage to the eye or of an infection such as latent glaucosis.

In eye fundus cameras which focus on the eye fundus in the naturally dilated state of the pupil, the eye is illuminated by infrared light and an image is formed on an infrared light image tube or the light sensing plane of an infrared video tube. The resulting infrared light image, which is equivalent to the visible light image of the eye fundus to be photographed on film, is electrically converted into a visible image and displayed. The operator focuses upon the eye fundus by operating focusing means on the basis of the sharpness of the thus produced image. However, the color of the eye fundus is such as to produce little contrast in response to infrared light. Furthermore if the eye fundus is inflamed due to an infection, it is difficult to obtain a clear image of objects such as veins. This makes focusing of the camera all the more difficult.

Another example of the eye fundus camera which focuses infrared light is disclosed in the U.S. Pat. No. 3,614,214 (Oct. 19, 1971). The eye fundus camera disclosed in this literature presents, beside the main body of the photographic system, an automatic optometer equipped with focussing means functionally engaged with the focussing means of the main body of the photographic system. This optometer presents a means for forming an infrared light beam alternatively directed along two different directions and a mark so as to project the image of the mark on the eye fundus by means of the two light beams. In case the image of the mark is out of focus, two images of the mark appear alternatively at the different places on the eye fundus. If the image of the mark is in focus two images of the mark appear alternatively the one over the other at the same place of the eye fundus. This image on the eye fundus, of the infrared mark is reprojected on two adjacent infrared photo detectors and the then produced currents are applied to a subtractor. The difference signal between the currents from both detectors, permits automatic control of the focussing means of the automatic optometer and therefore at the same time also the focussing means of the photographic system. The most important shortcoming of the above mentioned eye bottom camera is that it is impossible to determine the photographic view field during the focussing operation. In other words, it is impossible to confirm which part of the eye fundus is photographed. The shutter of the camera is automatically released, while the operator is not sure on which part of the eye fundus the image of the focusing mark is projected.

SUMMARY OF THE INVENTION

The purpose of the present invention is to offer an eye fundus camera equipped with a mechanism capable of focusing on the eye fundus in the naturally dilated state of the pupil of the eye to be inspected, by making use of a light not causing dilation and contraction of the pupil in such a way that not only it is easy to properly adjust the focus but also that it is possible to determine the photographic view field during focussing.

In this specification, light ineffective dilatation and contraction of the pupil of the eye to be inspected is to be understood to include weak visible light which is able to keep the pupil in the almost dilated state as well as invisible lights such as infrared light and ultraviolet light.

An embodiment of the eye fundus camera in accordance with the present invention comprises a photographic system, a projection system and an observation system. These three systems include a common objective lens. The photographic system registers the image of the eye fundus on the photographic film. The projection system projects an image of a certain determined shape of the mark on the eye fundus by means of the infrared light. The focussing means of the photographic system is functionally engaged with that of the projection system in such a manner both systems focus at the same time. The observation system receives the infrared light from the eye fundus so as to convert the image in the infrared light into the visible image.

DETAILED DESCRIPTION OF THE PREFERRED EMBODIMENTS

Figure 1:
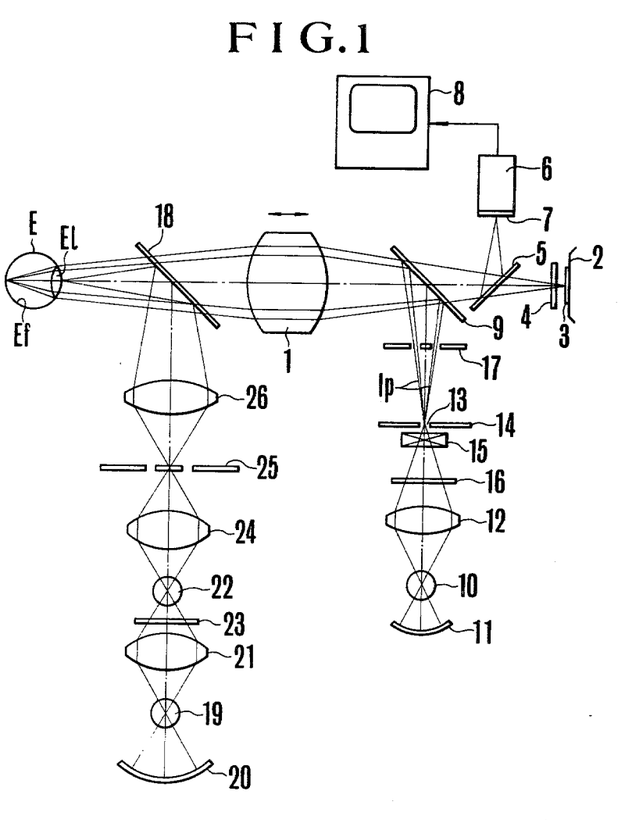
FIG. 1 shows an embodiment of the present invention.

In FIG. 1. a photographic lens 1 is mounted in a conventional lens barrel movable along a optical axis by means of helicoid mechanism by rotating the ring on a lens barrel. Arranged on the optical axis of the photographic lens 1, are the eye E to be inspected and the register plane 2 on which a photographic film 3 sensitive to the visible light is present. A focal plane shutter appears in the optical path in front of the photographic film 3. The shutter 4 is operated by means of a conventional shutter means used in a conventional photographic camera. This operating means controls not only the opening and closing of the shutter 4, but also the shutter speed. Obliquely in the optical path between the photographic lens 1 and the register plane 2, a first reflection member 5 such as cold filter reflects the infrared light and allows the visible light to pass through so as to divide the optical path into two. The infrared light reflected by means of the first reflection member 5 is directed toward the light sensing plane 7 of the video tube 6. The video tube 6 converts the image formed on the light sensing plane 7 by means of the infrared light into an electrical signal and applies it to the television image receiver 8. The television image receiver 8 displays the image formed on the light sensing plane 7 by means of the infrared image as visible image. A monitor television device such as one which comprises a video tube 6 and an image receiver 8 is already known.

Figure 4:
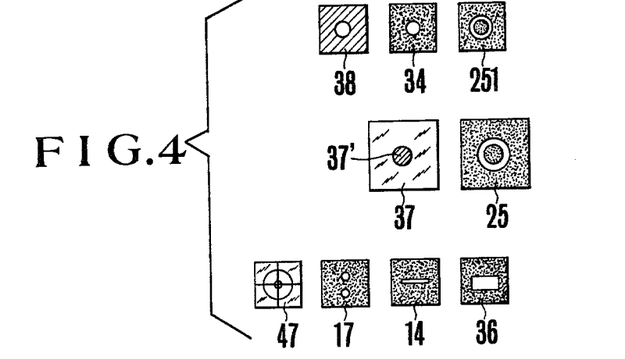
FIG. 4 shows optical members used in the embodiment of the present invention.

In the optical path before the first reflection member 5, but after the photographic lens 1, a second oblique reflection member 9 such as a semi transparent mirror partly reflects the incident light beam and partly allows the incident light beam to pass through, so as to branch the optical path. In the optical path branched by the reflecting plane of the second reflection member 9, appear a tungsten lamp 10, a concave mirror 11 and a condensor lens 12. A mark of predetermined shape is established at the position at which the light beam coming out of the tungsten lamp 10 is focused by means of the condenser lens 12. The mark 13 is a rectangular opening provided on the shading plate 14, as is shown in FIG. 4. Close to the mark 13 and in the optical path at the lamp side is a split image prism 15. This prism 15 consists of two adjacent transparent parts. The planes at which the light beam enters and/or goes out of the transparent parts are inclined along the different directions. In consequence, the light beam coming from the tangsten lamp 10 and entering the prism 15 is divided into two light beams directed along two different directions. By means of the effect of this prism 15, the light beams coming out of the two different but adjacent part of the mark 13 are directed along the different directions. The prism 15 can hereby be provided in the optical path opposite the tungsten light in view of the mark 13.

In the optical path between the mark 13 and the lamp 10, a filter 16 allows only the infrared light to pass through. Consequently, the light beam entering into and going out of the mark 13 is the infrared light. This filter can also be provided in the optical path opposite the tungsten lamp 10 in view of the mark.

A diaphragm or mask or slit 17 having two openings as is shown in FIG. 4 adjust the amount of the two light beams coming out of the mark 13.

A third reflection member 18 such as a semitransparent mirror obliquely in the optical path between the eye E to be inspected and the photographic lens 1, divide the optical path into two. In one of the branched optical paths a tungsten lamp 19, a concave mirror 20 and a condenser lens 21 are provided. At the position at which condenser lens 21 focuses the light beam coming from the tungsten lamp 19, a flash or speed light tube 22 produces a visible light flash by means of a conventional flash actuating control means while the shutter is open. In the optical path between the speed light tube 22 and the tungsten lamp 19, a filter 23 allows only the infrared light to pass through. A condenser lens 24 causes convergence of the light beam coming from the speed light tube 22 and the tungsten lamp 19 on the ring slit 25 (FIG. 4). The image of this ring slit 25 is formed on the pupil of the eye E to be inspected by means of the lens 26 through the third reflection member 18. Thus, a ring shaped light beam enters into the eye E to be inspected, so as to illuminate the eye fundus. The optical members from the third reflection member to the concave mirror 20 form the illumination system.

Thus, receiving two light beams from the mark 13 the photographic lens 1 projects the image of the mark 13 to the eye to be inspected. The photographic lens 1 and the optical members from the second reflection member 9 to the concave mirror 11 form the projection system.

Then the photographic lens 1 forms the image of the eye fundus Ef on the recording plane 2. The photographic lens 1 and the recording plane 2 form the photographic system.

Further, the photographic lens 1 forms the image in infrared light, of the eye fundus and of the image in infrared light, of the mark formed on the eye fundus by means of the above mentioned projection system on the light sensing plane 7 of the video tube 6. The photographic lens 1, the first reflection member 5, the video tube 6 and the image receiver 8 form the observation system.

The recording plane 2, the light sensing plane 7 and the mark 13 are arranged in such a manner that their lengths of the optical path from the photographic lens 1 are equal. Therefore, in case the image formed on the eye fundus Ef, of the mark 13 is in focus, the image formed on the recording plane 2 and the light sensing plane 7, of the eye fundus Ef and the image of the image of the mark on the eye fundus are also in focus.

Figure 6A:
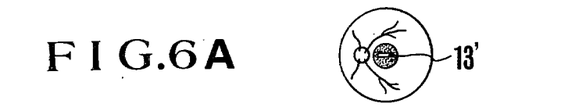
FIGS. 6A, 6B and 6C respectively show the image of the eye fundus and the mark indicated by the observation system.
Figure 6B:
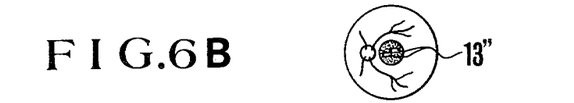
Figure 6C:
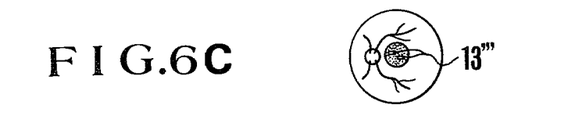

In case the image, of mark 13 projected on the eye fundus, of is out of focus, this image is separated by the effect of the split image prism 15 like 13'', 13''' as is shown in FIGS. 6B and 6C. In case the image is in focus, the image on the eye fundus, of the mark coincides with the original shape of the mark 13 like 13' as is shown in FIG. 6A (the images shown in FIGS. 6A, 6B and 6C are indicated as visible images by means of the image receivers 8). The focus adjustment of the projection system and the photographic system is made by translating the photographic lens 1 along the direction of the optical axis by means of the aforementioned helicoid mechanism. When the image of the mark enters into focus, the shutter 4 is opened while the speed light tube 22 is actuated in such a manner that the image in the visible light of the eye fundus in focus is recorded on the photographic film 3 arranged on the recording plane 2.

Figure 2:
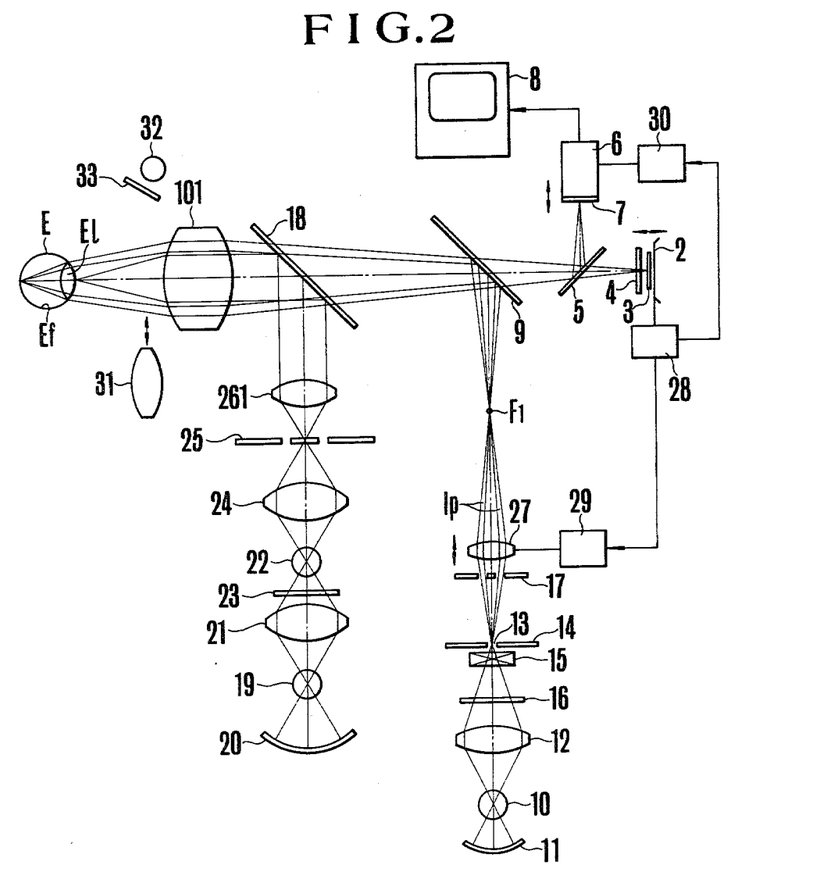
FIG. 2 shows another embodiment of the present invention.

FIG. 2 shows another embodiment of the present invention. The members in common with those of FIG. 1 bears the same figures.

In FIG. 2, the recording plane 2 is provided so as to be movable along the direction of the photographic optical path for easy focus adjustment of the photographic system. For example, this moving mechanism is so designed that the recording plane 2 and the shutter 4 are contained in one dark box. The dark box is mounted on the guide rail provided along the direction of the optical path in such a manner that the dark box is moved along the guide rail by means of the screw mechanism. A linear potentiometer 28 detects the amount of the movement of the above mentioned dark box, namely of the recording plane 2, along the direction of the guide rail, namely of the optical path. The electrical signal produced by the linear potentiometer 28 is conveyed to the first servo-motor 29 and the second servo-motor 30 in such a manner that the motors 29 and 30 are rotated along the direction corresponding to the direction of the movement of the recording plane 2 by the amount corresponding to the amount of the movement of the recording plane 2.

A relay lens forms the image of the mark 13 at the point $F_1$ in the optical path between the mark 13 and the second reflection member 9. The relay lens 27 is provided in a lens barrel so as to slide in the direction of the optical axis along the inner wall of the lens barrel. Thus the relay lens is translated by the first servo-motor 29 by means of a conventional mechanism for converting a rotary motion into a linear motion. The above potentiometer 28 and the first servo-motor 29 serve to translate the relay lens 27 in such a manner that the above mentioned recording plane 2 and the point $F_1$, namely the point at which the image of the mark 13 is formed by the relay lens 27 always are equidistant along an optical path from the photographic lens 101. The video tube 6 is provided so as to be movable along the guide rail provided along the optical path by means of a screw mechanism. Thus the second servo-motor 30 moves the video tube 6 by means of the screw mechanism. The linear potentiometer 28 and the second servo-motor 30 control the movement of the video tube 6 in such a manner that the light sensing plane 7 of the video tube 6 and the recording plane 2 are equidistant along the optical path from the photographic lens 101.

In case the image displayed by the image receiver 8 is separated as is shown in FIGS. 6B and 6C, it is sufficient for the operator to move the recording plane 2 forwards and backwards along the optical path, observing the displayed image in such a manner that the point $F_1$ assumes a conjugate position with the eye fundus Ef, so that the image of the mark eye fundus coincides with its original shape. Thus the photographic system automatically focuses on the eye fundus Ef.

In case of FIG. 2, the focus adjustment is not carried out by moving the photographic lens 101 along the optical axis. Thus the third reflection member 18 of the illumination system can be provided slantly arranged obliquely in the optical path after the photographic lens 101. However the image of the slit 25 is formed on the pupil of the eye E by means of the lenses 261 and 101. (In FIG. 1, the illumination would vary with the focus if the third reflection member 18 appeared at this position.)

In FIG. 2, includes an optical system which is not provided in FIG. 1. An auxiliary lens 31 serves for positioning the pupil, and is moved into and out of the optical path to the photographic lens 101 by mechanical means with a lever mechanism. When the auxiliary lens 31 is moved into the optical path, to the eye E to be inspected, the lenses 31 and 101 form the image of the pupil of the eye E to be inspected on the light sensing plane 7 of the video tube 6 with the first reflection member 5. A switch is closed in synchronism with the above mentioned mechanical means. The switch operates a tungsten lamp 32 located out of the optical path of the lens 101 and opposite the eye E to be inspected. A filter 33 allows only the infrared light from the lamp 32 to pass through to illuminate the pupil or the eye lid of the eye E to be inspected with the infrared light. In order to adjust the relation of the position of the optical system of the camera to that of the pupil of the eye E to be inspected, it is sufficient for the operator to switch off the lamps 10 and 19, light up the lamp 32, bring the auxiliary lens 31 into the optical path between the eye E to be inspected and the lens 101 and operate the conventional positioning means for adjusting the position and the direction of the main body containing the optical systems of the camera, and observe the image of the pupil displayed by the image receiver 8.

Figure 3:
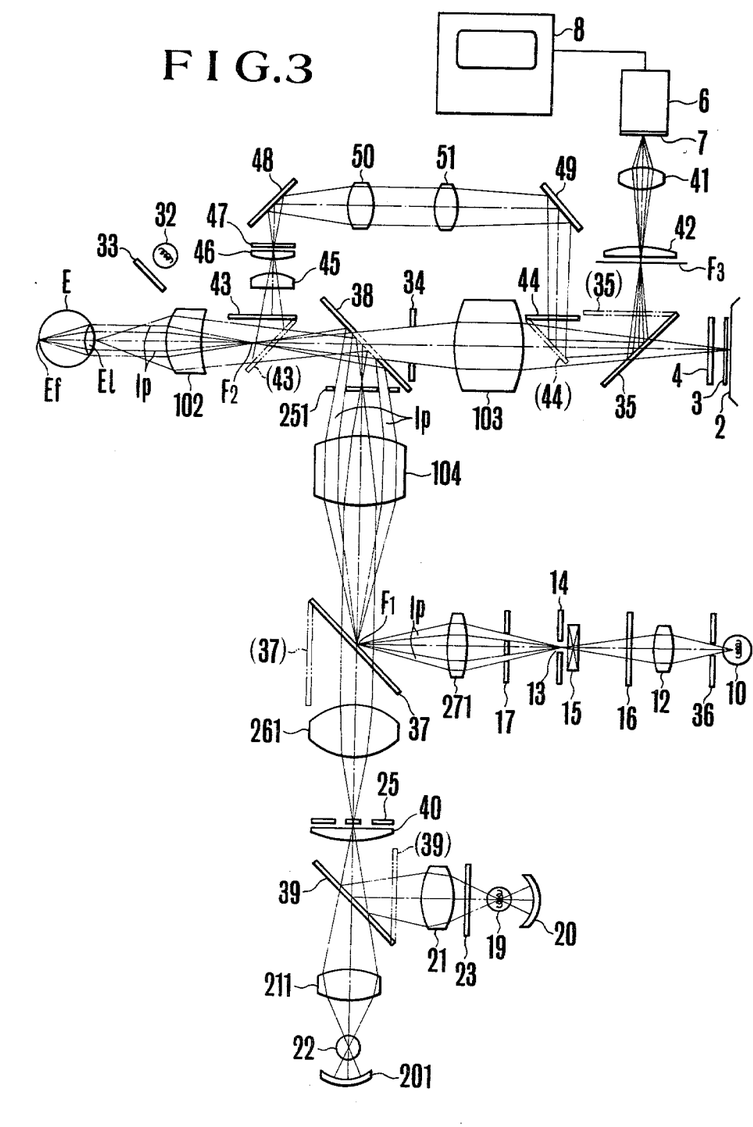
FIG. 3 shows further another embodiment of the present invention.

FIG. 3 shows the optical system of further another embodiment of the present invention.

Here, the photographic system is composed of an objective lens 102, a relay lens 103, the recording plane 2. The image of the eye fundus Ef of the eye E to be inspected is formed close to the focal plane by the lens 102 and reformed on the recording plane 2 and on the plane $F_3$ by the reversing mirror 35 and the relay lens 103. A photographic film 3 such as color film is placed on the recording plane 2, so as to record the image of the eye fundus Ef. The projection system includes the tungsten lamp 10, the diaphragm 36 with a rectangular opening (FIG. 4), the condenser lens 12, the infrared filter 16, the split image prism 15, the mark 13 with a predetermined shape, the slit 17 with two openings, a relay lens 271, an optical path dividing means (in the present embodiment a partially reflecting transparent plate with a reflecting film 37' on a small part of the transparent plate as is shown in FIG. 4), a relay lens 104, an optical path dividing means 38 (in the present embodiment a mirror with opening as is shown in FIG. 4), and an objective lens 102. In FIG. 3, the relay lenses 103 and 104 are optically equivalent to each other (namely their focal lengths are substantially equal to each other) and disposed symmetrically with reference to the mirror 38 with an opening.

The light beam coming out of the light source 10 through the diaphragm 36 is made to converge at the mark 13 by the condenser lens 12. The infrared filter is located between the lens 12 and the mark 13. Thus the light beam in the optical path of the projection system after the infrared filter 16 consists exclusively of the infrared light. The visible components are excluded from the light beam so that the eye E does not sense visible light beam from the projection system. In the neighborhood of the mark 13, the split image prism 15 is provided in such a manner that the infrared light beam having passed through the prism 15 and the mark 13 is divided into two beams so as to obtain an infrared light beam $I_p$.

Figure 5:
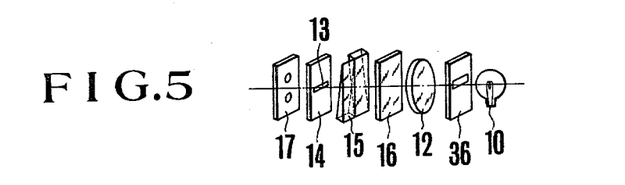
FIG. 5 shows a part of the photographic system in perspective view.

The arrangement from the light source 10 up to the slit with two opening is shown in FIG. 5, in perspective. The relay lens 271 forms the image of the mark 13 on the reflecting part 37' of the partically reflecting transparent plate 37. The image forming point $F_1$ is arranged at a position equivalent to that of the recording plane 2. (Hence, the image position conjugate with the recording plane for the lens 103 coincides with the image position conjugate with the image forming point $F_1$ for the lens 104.) (Also, in the present embodiment the relay lenses 103 and 104 are optically equivalent to each other and arranged symmetrically with reference to the mirror 38 with opening. The infrared light beam $I_p$ reflected by the plate 37, passes through the relay lens 104 and the slit of the ring slit 251 (to be explained later) and reflected by the mirror 38 with opening, converges at the focal point $F_2$ behind the objective lens 102 or in its neighborhood and then passes through the objective lens 102 and the crystalline lens El of the eye E so as to be projected on the eye fundus Ef. When the infrared light focusing beam $I_p$ converges precisely at the focal point $F_2$ behind the objective lens 102, the infrared light beam emerges from the objective lens 1 as a parallel beam. Therefore, when the eye E is focused at an infinite distance, the beam $I_p$ converged precisely on the eye fundus Ef in such a manner that an image with the same shape as that of the mark 13 is formed on the eye fundus Ef as is shown in FIG. 6A. If for some reasons such as the abnormal refraction of the eye E, the image of the mark 13 is not precisely formed on the eye fundus but is separated into two images 13″ and 13‴ shown in FIGS. 6B and 6C in accordance with the angle at which the images of the two openings of the slit 17 meet at a point on the eye fundus. In order to make the images 13″ and 13‴ of the mark 13 coincide with the original shape of the mark 13, it is sufficient to move the position at which relay lens 104 causes the infrared focusing light beam $I_p$ to converge along the optical axis by a proper amount from the focal point $F_2$ behind the objective lens 102. Now, the slit 17 with two openings is placed at the focal point behind the relay lens 271. The two openings are contained in the image of the slit formed by the relay lenses 104 and 271, of the ring slit 251 (to be explained later). Thus the straight line connecting the center of the one opening with that of the other opening lies on the diameter of the image of the ring slit 251. The dimension of the opening of the diaphragm 36 is determined in such a manner that the light beam divided into two by means of the split image prism 15 passes separately through the two openings of the mask 17 without causing the interference between each other. Therefore the two openings in the mask 17 are provided near the images of the opening of the diaphragm 36 formed by means of the condensor lens 12 and the split image prism 15.

The eye fundus illuminating system includes the tungsten lamp 19, the infrared light filter 23, the condensor lens 21, the reversing mirror 39 (a totally reflecting mirror), the electronic flash 22 operating in synchronism with the shutter 4 as is explained in accordance with FIG. 1, a condenser lens 21, the ring slit 25, a relay lens 261, and the ring slit 251. These operate together with the afore mentioned relay lens 104, the optical path dividing means 38 and the objective lens 102. The light beam coming from the illumination light source 19 for the eye fundus together with the light beam partially reflected by the concave mirror 20 converge on the ring slit 25, after passing through the condenser lens 21, the reversing mirror 39 and the field lens 40. The light beam passing through the ring slit 25 is converted into a parallel light beam by means of the relay lens 261 whose rear focus is located at the center of the ring slit 25. The beam then passes through the transparent part of the partially reflecting transparent plate 37 in such a manner that its image is formed on the ring slit 251 placed at the front focal plane of the relay lens 104. The beam is then reflected by means of the mirror 38 with opening provided slantly in the optical path of the photographic system and focused by the objective lens 102, on the eye lid of the eye E to be inspected. The image of the ring slit 25 is formed on the ring slit 251 by means of the lenses 261 and 104 in such a manner that the image of the ring of the ring slit 25 coincides with the ring of the ring slit 251. The image of the ring slit 251 is formed on the eye lid of the eye E to be inspected, by means of the objective lens 102. Between the lenses 261 and 104 the light beam for illumination is a parallel beam. The lenses 104 and 103 are optically equivalent to each other and arranged symmetrically to each other with reference to the mirror 38 with opening. In consequence the part corresponding to the central part of the ring of the image of the eye fundus formed on the plane $F_3$ is dark, so that the contrast of the image of the mark projected at this part is great. Further, by providing the ring slits 25 and 251 in the optical path of the light beam for illumination, the light beam reflected by the objective lens and the cornea is prevented from reaching the recording plane 2 and the plane 7 due to the principle of the ordinary ring illumination method. Further, because between the light source 19 for illuminating the eye fundus and the condensor lens 21 an infrared light filter 23 is provided, the light beam illuminating the eye fundus Ef is the infrared light which is not sensed by the eye as explained above.

Member 35 is an optical path dividing means (in the present embodiment a reversing mirror), 41 a relay lens, 6 the image receiver for the infrared light, 8 the television. These four members form the observation system together with the above mentioned objective lens 102 and the relay lens 103. When the photographic system focuses on the eye fundus Ef of the eye E being focussed at an infinite distance, the image of the eye fundus is formed at the focal point $F_2$ behind the objective lens 102 or in its neighborhood. It then passes through the opening of the mirror 38. The relay lens then focuses the image on the recording plane 2 or on the plane $F_3$ which is symmetrical to the recording plane 2 with reference to the reversing mirror 35 in the optical path of the photographic system.

During the focussing operation, the reversing mirror 35 is swung into the optical path of the photographic system. In consequence, the infrared light beam coming from the projection system and the illumination system and reflected on the eye fundus Ef returns through the objective lens 102, passes through the relay lens 103 and is reflected by the reversing mirror 35 so that its image is formed on the plane $F_3$, then further passes through the field lens 42 and a relay lens 41 forms its image on the light sensing plane 7 of the infrared-light video tube 6. The IR video tube 6 converts the infrared information into an electrical signal which is applied to the television 8. The television 8 converts the above mentioned electrical signal into television picture, so as to display the infrared light image as the visible image.

Instead of the video tube 6 and the television 8, other means such as an infrared image tube for converting the infrared image into visible image can also be utilized.

As explained above, the projection system and the illumination system have a common optical path with the photographic system through the open mirror 38 while the observation system has a common optical path with the photographic system through the reversing mirror 35.

The reversing mirrors 35, 37 and 39 are movable out of the optical paths and to the positions shown by the dotted lines with the operation of the shutter 4. For example, the mirrors, 35, 37 and 39 are fixed on the rotary shafts at the part at which the full lines cross with the dotted lines. Each rotary shaft is connected with a motor shaft connected with the input switch operated by means of a conventional release for operating shutter 4. When the release mechanism begins to open the shutter 4 each mirror is moved to the position shown in dotted lines. When the shutter 4 finishes closing each mirror is brought into the position shown in full line.

Further, the relay lens 104 is movable along the optical axis by means of the same mechanism as in case of the lens 1 in FIG. 1. Its movement can be detected by means of the similar linear potentiometer as in case of the recording plane 2 in FIG. 2. Further, the relay lens 103 movable along the optical axis by means of a servo-motor through a similar mechanism as in case of the lens 27 shown in FIG. 2. This servo-motor is controlled by means of the aforementioned potentiometer in such a manner that the relay lens 103 and the relay lens 104 are moved along optically corresponding directions by the same optical amount. Thus in case, the relay lens 104 is moved in such a manner that the image of the mark 13 on the eye fundus Ef coincides with the original shape of the mark, the photographic system automatically is in focus. (At the time of this focus adjustment it goes without saying that each reversing mirror 35, 37 and 39 is at the position shown in full line, whereby the image of the eye fundus Ef and that of the image of the mark 13 on the eye fundus Ef are indicated by the television 8.) However, if the illumination eye fundus system and the focusing mark projecting system share a common relay lens 104, as shown in FIG. 3, the illuminated of the eye fundus is varied by moving the relay lens 104. In consequence, it is desirable that the focus adjusting means be similar to that shown in FIG. 2. Namely, the recording plane 2 is provided so as to be movable along the direction of the optical path, whereby its movement is detected by the linear potentiometer. Further, the members from the reversing mirror 37 up to the lamp 10 is contained in a cylindrical body (not shown) which is mounted on a guide rail (not shown) provided along the direction of the optical axis of the relay lens 104, so as to be movable along the guide rail by means of a screw mechanism (not shown). This screw mechanism is driven by means of a servo-motor, e.g. 29, controlled by the above mentioned potentiometer e.g. 28, in such a manner that the point $F_1$ and the recording plane 2 are moved along optically in the same direction by an optically equivalent amount. On the other hand, the members from the field lens 42 up to the video tube 6 are contained in a cylindrical body not shown which is moved by means of the same mechanism as explained above. (It is also possible to connect a linear potentiometer with the above mentioned cylindrical body, so as to drive the recording plane 2 and the video tube 6 by means of a servo-motor being controlled by this potentiometer.) In consequence, by moving the recording plane 2 by a certain proper amount while confirming the image displayed on the television, it is possible to make the image projected on the eye fundus Ef, of the mark 13 coincide with the original shape of the mark 13, at which point the photographic system is in focus. Further the monitor television 8 not only displays the image of the mark, but also the image of the eye fundus illuminated over a wide range by the illumination system for the eye fundus. This makes it possible for the operator to determine the photographic view field while observing the images displayed. He determines the view field by changing the relative direction of the optical axis of the photographic system to the eye E. He does this, for example, by changing the direction of the fixed eye toward the eye to be inspected of which viewing direction is fixed by means of a conventional camera positioning means or the direction of the eye directing target at which the patient is to look, toward the eye.

After focussing and determining the photographic view field, the reversing mirrors 35, 39 and the partially reflecting transparent plate 37 are moved out of the optical path to the positions shown in broken lines (35), (37) and (39), the shutter is then opened and then the eye fundus Ef is illuminated with visible light by operating the electronic flash or speed light source 22 so as to expose the color film 3 to the visible light. It is possible to place an infrared light filter in the optical path of light from the speed light source 22, so as to illuminate the eye fundus Ef with infrared light beam of high intensity. In this case, the film 3 must be a film sensitive to infrared light, which is, in general, a monochromatic film. However to examine the eye fundus precisely, it is more desirable to examine a color than a monochromatic picture.

On the other hand, in order not to make use of any pupil dilating agent, the eye E must be shaded from visible light at the time of focus adjustment of the camera and the determination of the photographic view field. In consequence before the focus adjustment and the determination of the photographic view field, it is necessary to use invisible light to carry out the pupil positioning. Pupil positioning involves adjustment of the direction and the position of the pupil, so as to keep the objective lens 102 at a certain determined distance from the pupil, thereby preventing the recording plane 2 from the undesirable light reflected from the pupil. An example of the means for the above is explained with respect to FIG. 2.

In the embodiment shown in FIG. 3, the positioning of the pupil is carried out by means of infrared light similar to the case shown in FIG. 2. Member 32 is a tungsten lamp which faces the eye E through the infrared filter 33. Reversing mirrors 43 and 44 (totally reflecting mirrors) are brought into the optical path (as shown in dotted line) between the objective lens 102 and the relay lens 103, and between the relay lens 103 and the recording plane 2 at the time of the positioning of the pupil, so as to form an optical path bypassing the relay lens 103. The reversing mirrors 43 and 44 are fixed on their rotary shafts which are engaged with each other by means of a gear mechanism so as to be rotated by means of a knob provided outside of the camera body. Member 45 is an auxiliary objective lens, 46 a field lens and 47 a transparent plate defining a cross mark as is shown in FIG. 4 on which the image of the eye E is formed by means of the objective lens 102, the auxiliary objective lens and the field lens 46. Members 48 and 49 are the mirrors serving to bend the optical path of the pupil positioning system. Members 50 and 51 are the relay lenses serving to reform the image formed on the above mentioned plate 47, of the pupil on the plane $F_3$ symmetrical to the recording plane 2 with reference to the reversing mirror 35. The infrared image of the pupil of the eye E to be inspected is reformed on the light sensing plane 7 of the video tube 6 by means of the relay lens 41, so that the image of the pupil is displayed on the monitor television 8. The above mentioned embodiment in which the recording plane 2 is moved for the focus adjustment of the eye fundus is designed in such a manner that although the above mentioned plane $F_3$ is also moved, the lens 51 is moved along the optical axis so as to always form the image of the pupil on the plane $F_3$. This is done by the same mechanism as the lens 27 in FIG. 2. The lens 51 is moved by means of a servo-motor being controlled by the potentiometer for detecting the position of the recording plane 2. In consequence, the image of the pupil displayed by the monitor television 8 is always in focus. Thus it is sufficient for the operator to operate a conventional camera positioning means for changing the relative position of the camera toward the pupil of the eye E, while observing the image of the mark of the plate 47 and of the pupil displayed on the monitor television 8 and considering the position of the image of the pupil toward that of the mark of the plate 47 displayed on the monitor television 8.

According to another embodiment shown in FIGS. 1, 2 and 3 filters allowing only the ultraviolet light are adopted instead of the filters 16, 23 and 33 in FIGS. 1, 2, and 3, and a video tube producing electrical signal in response to the ultraviolet light is used instead of the video tube 6. This makes it possible to adjust the focus and determine the photographic view field of the camera by means of invisible ultraviolet light.

Further, there are other embodiments in which instead of the filters 16, 23 and 33 light reducing filters such as ND filters are adopted or light sources 10, 19 and 32 which produce weak visible light are used. For projecting the image of the mark 13 and of the ring slit to the eye to be inspected, use is made of a light which contains the spectrum range of the visible light but is too weak to cause dilatation and the contraction of the pupil of the eye to be inspected. Other embodiments, instead of the monitor television means utilized a conventional image intensifier which makes use of the photo multiplication effect due to secondary-electron emission of the chain reaction of electron-emissive material in an electrical field. Its light sensing plane is placed at the same position as that of the light sensing plane 7 of the video tube 6. This image intensifier amplifies an image of the visible light, which comes from the eye fundus of the eye to be inspected but is so weak that the eye can not sense it directly, into a bright image clearly visible to the eye.

What is claimed is:

1. An eye fundus camera, comprising:
   an optical system including plane means defining a recording plane, optical means between the eye to be inspected and the recording plane for forming an image of the eye fundus of the eye to be inspected on the recording plane;
   illuminating means for illuminating the fundus of the eye to be inspected with light ineffective to cause contraction of the pupil of the eye;
   mark means for defining a mark having a predetermined shape;
   projecting means holding the mark means and forming a light beam ineffective to cause contraction of the pupil of the eye to be inspected for projecting an image of the mark, said optical means being arranged relative to said projecting means for forming the image of the mark on the eye fundus;
   focusing means coupled to said optical system and projecting means for simultaneously adjusting the focus of the image of the eye fundus on the recording plane and the focus of the image of the mark upon the eye fundus; and
   display means optically coupled with said optical system for forming a visible image of the mark, said display means including sensing means defining a sensing plane for sensing light ineffective to cause contraction of the pupil and coming from the eye fundus through said optical means, and converting means for converting the image formed on the light sensing plane into a visible image.

2. An eye fundus camera according to claim 1, wherein said optical system and said projecting system presenting at least partially common optical path, the eye to be inspected existing in said common optical path.

3. An eye fundus camera according to claim 2, wherein said projecting means includes the optical means of said optical system.

4. An eye fundus camera according to claim 3, wherein said optical system being provided so as to be movable along the direction of the optical axis in such a manner that the focus of the image of the eye fundus formed on the recording medium and that of the image of the mark formed on the eye fundus by means of a light not causing the reaction of the mechanism for contracting of the pupil of the eye to be inspected can be adjusted.

5. An eye fundus camera according to claim 1, wherein said focussing means consisting of a first focussing portion coupled to the plane means for adjusting the focus of the image of the eye fundus formed on said recording medium and a second focussing portion coupled to the sensing means for adjusting the focus of the image of the mark formed on the eye fundus, said first and said second focussing portions being functionally engaged with each other in such a manner that the focus of the image of the eye fundus formed on the recording medium and that of the image of the mark formed on the eye fundus can be adjusted at the same time.

6. An eye fundus camera according to claim 5, wherein said recording plane on which said recording medium is to be provided being provided so as to be movable along the direction of the optical axis, said recording plane being moved and adjusted by means of said first focussing means.

7. An eye fundus camera according to claim 5, wherein said projecting means includes a lens for forming the image of the mark at a position in the optical path to the eye to be inspected, and said second focussing means moves the last-mentioned image of the mark along the direction of the last-mentioned optical path.

8. An eye fundus camera according to claim 1, wherein said display means is a monitor television means.

9. An eye fundus camera according to claim 1, wherein said display means is an image intensifier.

10. An eye fundus camera according to claim 1, wherein said projecting means includes a light beam splitting means in the optical path of said projecting means corresponding to the mark into a plural number of different rays.

11. A camera as in claim 1, wherein the light beam projected by said projecting means is infrared light.

12. A camera as in claim 1, wherein the light beam from said projecting means is ultraviolet light.

13. A camera as in claim 1, wherein the light beam from said projecting means covers the visible spectrum but is sufficiently weak to be ineffective to cause contraction of the pupil.

14. A camera as in claim 3, wherein said optical means forms an optical axis and wherein said focusing means moves said optical means along the optical axis for focusing the image of the mark on the eye fundus simultaneously with the image of the eye fundus upon the recording plane.

15. An eye fundus camera according to claim 1, wherein said recording plane on said plane forming means is movable along the direction of the optical axis by means of said first focusing means, said projecting means for projecting the image of said mark on the eye fundus having a lens for forming the image of said mark at a position in the main optical path to the eye to be inspected, said image of said mark formed in the optical path being movable along the direction of the main optical path by means of said second focusing means.

16. An eye fundus camera according to claim 11, wherein the illuminating means comprises a photographic light source and an observing light source both arranged along an optical axis from the eye to be inspected, and a filter between the light sources for shielding visible light and transmitting infrared light.

17. An eye fundus camera comprising:
- a lens system forming a main optical path to an eye fundus to be inspected and receiving light from the eye fundus;
- optical dividing means in the main optical path for forming first, second, and third auxiliary optical paths;
- plane forming means forming a recording plane in the first auxiliary path for holding a recording medium so that the lens system can form an image theron;
- display means having a sensing plane in said second auxiliary optical path for sensing the light from the eye fundus passing through said lens system and converting the image formed on said sensing plane into a visible image;
- mark defining means in the third auxiliary optical path for defining a mark with a given shape;
- projecting means in the third optical path for projecting the image of the mark onto the eye fundus with infrared light;
- light beam dividing means in the third auxiliary optical path for splitting the mark being projected onto the eye fundus into a plurality of different parts and for directing the parts along respectively different directions while the mark is projected on the eye fundus;
- said display means and said plane forming means forming a first arrangement and said lens system forming a second arrangement, said lens system and said optical dividing means forming an image of the eye fundus upon the recording plane and forming an image of the mark projected upon the eye fundus upon the sensing plane when the projecting means projects the image of the mark on the eye fundus;
- focusing means coupled to one of the arrangements for simultaneously adjusting the focus of the image of the eye fundus formed on the recording plane and the image of the mark on the eye fundus formed on the display means on the basis of the focus of the image of the mark on the eye fundus, and for separating the parts of the mark when the image of the eye fundus is out of focus and for causing the parts of the mark to assume the original shape of the mark when the image of the eye fundus is in focus.

18. An eye fundus camera according to claim 17, wherein said lens system is movable along the direction of the main optical path for adjusting the focus of the image of the eye fundus formed on said recording plane and the image of the mark formed on the eye fundus by means of the infrared light, and said lens system is coupled to said focusing means.

19. An eye fundus camera according to claim 17, wherein said focusing means includes a first focusing means coupled to said plane forming means for adjusting the focus of the image of the eye fundus formed on said recording medium and a second focusing means coupled to said projecting means for adjusting the focus of the image of said mark formed on the eye fundus, said first and said second focusing means being functionally engaged for simultaneous adjustment of the focus of the image of the eye fundus formed on said recording medium and the focus of the image of said mark formed on the eye fundus.

20. An eye fundus camera according to claim 17, wherein said projecting means includes an infrared light source, said mark defining means having a masking plate with an opening of predetermined shape, the light beam passing through the opening from the light source being projected on the eye fundus.

21. An eye fundus camera according to claim 17, wherein said light beam dividing means is a split image prism.

22. An eye fundus camera according to claim 17, wherein said projecting means includes an infrared light source, said mark defining means having a shading plate with an opening of predetermined shape defining the mark, the light beam passing through the opening from the light source being projected on the eye fundus,
- said light beam dividing means being a split image prism in the path of light from the opening.

23. An eye fundus camera according to claim 17, wherein said display means includes monitor television means having an infrared light sensitive video tube.

24. An eye fundus camera according to claim 18, wherein said display means is a monitor television means having a video tube sensitive to infrared light.

25. An eye fundus camera according to claim 18, wherein said mark forming means includes a plate having an opening of predetermined shape, said projecting means comprising a light source for illuminating said mark and a split image prism between the plate and said light source.

26. An eye fundus camera comprising:
- an objective lens facing the eye to be inspected, and forming a main optical path,
- first optical path dividing means located on the main optical path on the side of the objective lens remote from the eye for dividing the optical path into the first and the second auxiliary optical paths,
- a first relay lens provided in said first auxiliary optical path,
- second optical path dividing means located on the first auxiliary path on the side of the relay lens more remote from the eye for dividing said first auxiliary optical path into the third and the fourth auxiliary optical paths,
- plane forming means in the third auxiliary optical path for defining a recording plane on which a recording medium is to be provided and on which the image of the eye fundus can be formed by said objective lens and said first relay lens,
- first focusing means coupled to said plane forming means for adjusting the focus of the image of the eye fundus formed on said recording means,
- mark defining means in the second auxiliary optical path for forming a mark with a predetermined shape,
- projecting means in the second auxiliary optical path for projecting the image of the mark on the eye fundus with infrared light along said second auxiliary optical path and through said objective lens, said projecting means including a second relay lens in the second optical path between said objective lens and the mark,
- second focusing means coupled to said projecting means for adjusting the focus of the image of the mark formed on the eye fundus, said first focusing means and the second focusing means being functionally engaged with each other for simultaneously focusing the image of the eye fundus formed on said recording medium and the image of the mark formed on the eye fundus, display means including a light sensing plane in fourth auxiliary optical path for sensing the infrared light coming from the eye fundus through said objective lens and said first relay lens and converting the infrared image formed on said light sensing plane into a visible image.

27. An eye fundus camera according to claim 26, wherein said first relay lens and said second relay lens are optically equivalent to each other.

28. An eye fundus camera according to claim 26, wherein said first relay lens is movable by said first focusing means along the direction of the optical axis, said second relay means being movable along the direction of the optical axis by said second focusing means.

29. An eye fundus camera according to claim 26, wherein said plane defining means is movable by said first focusing means along the direction of the main optical axis, said projecting means having a lens for forming the image of said mark at a position in the main optical path on the side of said second relay lens remote from the eye to be inspected, said image of said mark formed in the optical path being movable along said second auxiliary optical path by said second focusing means.

30. An eye fundus camera comprising:
- an objective lens facing the eye to be inspected and forming a main optical path;
- a first optical path dividing means in the main optical path on the side of the objective lens remote from the eye for dividing the main optical path and forming first and second auxiliary optical paths;
- a first relay lens in said first auxiliary optical path;
- second optical path dividing means in the first auxiliary optical path on the side of the first relay lens remote from the object to be inspected for dividing the first auxiliary optical path and forming third and fourth auxiliary optical paths;
- plane defining means in the third auxiliary optical path for forming a recording plane to receive an image of the eye fundus and being movable along the direction of the third auxiliary optical path;
- said objective lens and said relay lens being arranged to form an image of the eye fundus on said recording plane;
- first focusing means coupled to said plane defining means for adjusting the focus of the image of the eye fundus on said recording plane;
- mark forming means in said second auxiliary optical path for forming a mark having a predetermined shape;
- projecting means in said second auxiliary optical path for projecting the image of the mark on the eye fundus with infrared light along the second auxiliary optical path and through said objective lens;
- said projecting means including a lens for forming the image of the mark at a position in said second auxiliary optical path; said projecting means including a second relay lens optically equivalent to said first relay lens for projecting the image of said mark formed by said lens on the eye fundus;
- second focusing means coupled to said projecting means for moving the image of said mark formed in said second auxiliary optical path so as to adjust the focus of the image of the mark formed on the eye fundus, said first focusing means and said second focusing means being functionally connected with each other for simultaneously focusing the image of the eye fundus formed on said recording medium and the image of said mark formed on the eye fundus;
- display means in said fourth auxiliary optical path and having light sensing means along a plane for sensing infrared light coming from the eye fundus through the objective lens and said first relay lens and for converting the infrared image formed on the light sensing plane into a visible image.

* * * * *